United States Patent [19]

Bryant et al.

[11] Patent Number: 4,927,624

[45] Date of Patent: May 22, 1990

[54] CLAY MAGNETIC RESONANCE CONTRAST AGENTS FOR GASTROINTESTINAL COMSUMPTION OR INTRODUCTION

[75] Inventors: Robert G. Bryant, Pittsford; Jay J. Listinsky, Rochester, both of N.Y.

[73] Assignee: The University of Rochester, Rochester, N.Y.

[21] Appl. No.: 123,007

[22] Filed: Nov. 19, 1987

[51] Int. Cl.$^5$ ..................... A61K 49/00; G01N 24/00
[52] U.S. Cl. ......................................... 424/9; 436/173
[58] Field of Search ................... 424/9; 128/653, 654; 436/173

[56] References Cited

U.S. PATENT DOCUMENTS

| | | | |
|---|---|---|---|
| 4,615,879 | 10/1986 | Runge | 424/9 |
| 4,639,364 | 1/1987 | Hoey | 424/9 |
| 4,719,098 | 1/1988 | Weinmann et al. | 424/9 |
| 4,731,239 | 3/1988 | Gordon | 424/9 |

OTHER PUBLICATIONS

Sigma, Price List, Feb. 1982, p. 429.
Hackh's Chemical Dictionary, Fourth Edition, Grant (ed.), (1972), McGraw-Hill Book Co., New York, pp. 369, 437–438.
Physicians' Desk Reference, 35 Edition, (1981), p. 112, Kaopectate.
Young et al., J. Comput. Tomog. 5: 543–549, (1981).
Newhouse et al., Radiology, Jan. 1982, p. 246, vol. 142, No. 1.
Wesbey et al., Radiology, 149: 175–180, Oct. 1983.
Kornmesser et al., Proc. Soc. Res. Med. 5: 1522–1523 (1986).
Barnhart et al., Proc. Soc. Res. Med., 5:1520–1521 (1986).
Zabel et al., Proc. Soc. Res. Med., 5:259–260 (1986).
Hahn et al., Proc. Soc. Res. Med., 5:1537–1538 (1986).
Edelman et al., Radiology 1986, 161(P):314, (1986).
Mattrey et al., AJR 148: 1259–1263, Jun. 1987.

*Primary Examiner*—Robert J. Warden
*Assistant Examiner*—Jack Spiegel
*Attorney, Agent, or Firm*—Martin LuKacher

[57] ABSTRACT

Contrast medium compositions for delineation of bowel during magnetic resonance imaging (MRI) of the abdomen are provided for oral or rectal administration. The compositions consist of aqueous suspensions of clay in finely-divided particles which expose a large surface area to the suspending water and impose a condition of dynamic anisotropy upon the adjacent water, resulting in reduction predominantly in the transverse relaxation time of the water and subsequent loss of signal from the bowel lumen.

7 Claims, 3 Drawing Sheets

CLAY MAGNETIC RESONANCE CONTRAST AGENTS FOR GASTROINTESTINAL COMSUMPTION OR INTRODUCTION

DESCRIPTION

1. Field of the Invention

The field of the invention is that of nuclear magnetic resonance (MR) imaging for diagnosis of disease in human patients, and the contrast-enhancing agents used to improve the diagnostic accuracy of the examination. In particular, this invention is concerned with contrast agents which may be administered either by mouth or by enema for identification, delineation or examination of the gastrointestinal tract.

2. Background and Prior Art

Magnetic resonance imaging (MRI) has emerged in recent years as a powerful non-invasive method for examination of patients with known or suspected disease. The ability of MR imaging to discriminate among different soft tissues makes it an exceedingly effective diagnostic test for many abnormalities, and the lack of ionizing radiation makes MR an attractive alternative to X-ray examinations such as computerized axial tomography (CAT scan). The role of MR in diagnosis of neurologic disease is well-recognized (see, for example, the Statement of the Consensus Development Conference on Magnetic Resonance Imaging held at the National Institutes of Health, Oct. 26-28, 1987). Many abnormalities in the brain and spinal cord can be diagnosed without the need for administration of diagnostic drugs to the patient.

As experience with abdominal MRI has accumulated, however, it has become apparent that the accuracy of these studies would be greatly improved by the use of a contrast agent to distinguish bowel from adjacent tissues. This need arises because the contents of the bowel will depend upon diet and other unpredictable factors, and therefore the appearance of bowel on MR images will be unpredictable. Frequently, loops of bowel can have the appearance of tumors, abnormal lymph nodes, or inflamed tissue. Alternatively, tumors and inflammatory disease may be overlooked on MR images because these diseases may mimic normal bowel. The upper abdomen is a problematic area because the pancreas is adjacent to the stomach and duodenum. The latter two organs may obscure a tumor in the pancreas or may mimic the appearance of a tumor when none is present. Inaccurate evaluation of bowel on MR images may have three unfortunate outcomes, i.e., inaccurate diagnosis, inadequate assessment of spread of disease, and inaccurate assessment of the results of therapy.

A number of agents have been tried in humans for the purpose of distinguishing bowel from adjacent tissues. These agents have not entered widespread use due to various undesirable effects at doses required for imaging. Ferric chloride allowed visualization of the stomach presumably due to reduction of $T_1$. Young et al., *Comput. Tomogr.* 5:543-549 (1981). Gastrointestinal absorption of iron and gastrointestinal irritation limit the usefulness of this agent. Mineral oil increases signal from bowel by maintaining high proton density within bowel. Newhouse et al., *Radiology* 142:246 (1982). Potential toxicity at doses for imaging preclude this agent's use. Ferric ammonium citrate (found in Geritol) causes the bowel lumen to become bright, due to reduced $T_1$. Wesbey et al., *Radiology* 149:175, 1983. This agent causes the bowel to resemble fat, which may be confusing, and also may lead to worsening of image-degrading artifacts produced by motion of the high-signal intensity fluid within the bowel. A variety of additional agents have been employed either in human volunteers or in animals. These are novel agents in general and their safety as contrast agents remains to be established. Representative agents and references are as follows. Gadolinium-DTPA in aqueous solution produces bright signal from bowel. Kornmesser et al., *Proc Soc Magn Res Med* 5:1522-1523, 1986. Manganese solutions have been employed by oral administration. Barnhart et al., *Proc Soc Magn Res Med* 5:1520-1521, 1986. Nonabsorbable iron resins produce decreased signal from bowel. Zabel et al., *Proc Soc Magn Res Med* 5:259-260, 1986. Magnetite particles in suspension reduce the signal from bowel. Hahn et al., *Pro Soc Magn Res Med* 5:1537-1539, 1986; Edelman et al., *Radiology* 161(P):314, 1986. Perfluorocarbon compounds contain no protons and result in very low signal intensity from bowel. Mattrey et al., *AJR* 148:1259-1263, 1987. The toxicity of paramagnetic metals such as gadolinium can be reduced by preparing metal compounds in solid particulate form and suspending them in a fluid according to the patent to Runge et al., U.S. Pat. No. 4,615,879. (See the paragraph bridging Columns 4 and 5 of this patent).

The state of the prior art is briefly summarized as follows. Paramagnetic contrast agents are toxic and must be rendered less toxic by one of several chemical manipulations in order to be acceptable for trial in humans. In addition, these agents generally produce high-signal images which may cause bowel to be confused with surrounding tissues, particularly tissues that contain fat. Superparamagnetic particles have desirable contrast properties for purposes of bowel imaging. Their long-term effects are unknown and their safety in human use remains to be established. Perfluorocarbon agents also have desirable contrast properties and appear to be safe but are expensive to produce. A need exists for a bowel contrast agent which is nontoxic and inexpensive while providing high contrast between bowel and the surrounding tissues.

BRIEF SUMMARY OF THE INVENTION

In proton MR imaging, tissue signal intensities will depend principally upon the $T_1$, $T_2$, and proton density of each individual tissue. Contrast between two tissues on MR images will result if the tissues possess differences in one or more of the three parameters listed above. Paramagnetic contrast agents have been used most effectively to reduce the spin-lattice ($T_1$) relaxation times. In the context of abdominal MR studies, these agents produce bright signals from inside the bowel. Superparamagnetic particles produce bowel contrast mainly by reducing the spin-spin ($T_2$) relaxation times. This strategy will cause bowel to appear dark which is preferable for avoidance of confusing images and artifacts from moving bowel. Perfluorocarbon fluids cause bowel to appear dark due to reduction in proton density of the bowel contents.

In accordance with the present invention, a new method is provided by which bowel may be caused to appear dark on MR images. The invention is based on the discovery that contrast compositions which consist essentially of clay can be used to change the magnetic response of the cavity of the bowel and thereby cause it to appear markedly different from surrounding tissues on MR images. The composition is free of paramagnetic materials.

The method of the invention comprises administration to the patient of a composition which consists essentially of pharmaceutically acceptable clay. Such compositions may be administered either by oral or rectal route. Certain of these clays are known to be essentially nontoxic and nonabsorbable on the basis of many years of basic and clinical research. Two clays in particular, kaolin and bentonite, are classified by the Food and Drug Administration as "Generally Recognized As Safe" (GRAS). Federal Register Vol. 45, No. 13, Jan. 18, 1980.

According to the mechanism of the present invention, the bowel contrast which appears on MR images is due to the clay particles in aqueous suspension. These particles create local environments which induce changes in the motions of adjacent molecules of water. These changes in water motion cause reductions in spin-spin ($T_2$) relaxation times and, to a lesser extent, reductions in the spin-lattice $T_1$ relaxation times. These actions occur even though the clay agents are diamagnetic. There is no report in the prior art of an MR contrast agent which is diamagnetic and operates by changing the relaxation properties of the water spins.

DETAILED DESCRIPTION

The clay minerals are a class of materials generally considered as layered aluminosilicates. The clay minerals incorporate a number of subclasses such as the kaolins, serpentines, pyrophillites, smectites or montmorillonites, vermiculaites, illites, micas and chlorites. The detailed structures of these materials differ in the number of and structures of the layers and the nature of the interactions with water. A number of clay minerals will be useful in the process of this invention to change the nuclear spin relaxation properties of the liquid in contact with the materials. The safest materials are those devoid of heavy metal contamination. Two materials have been studied extensively in the context of this invention; kaolin and bentonite as a representative of the montmorillonite class of minerals. Both are effective water proton spin relaxation agents based on the surface effects in modifying the water molecule dynamics which govern both longitudinal and transverse spin relaxation rates. The efficiency and basic mechanisms for these two materials differ somewhat because kaolin does not swell in the presence of water, but the montmorillonites do; that is, the interlayer spacing increases with water content as water intercallates between the aluminosilicate layers. In the limit of very high water content, the montmorillonites such as bentonite form a gel.

Figure 1:
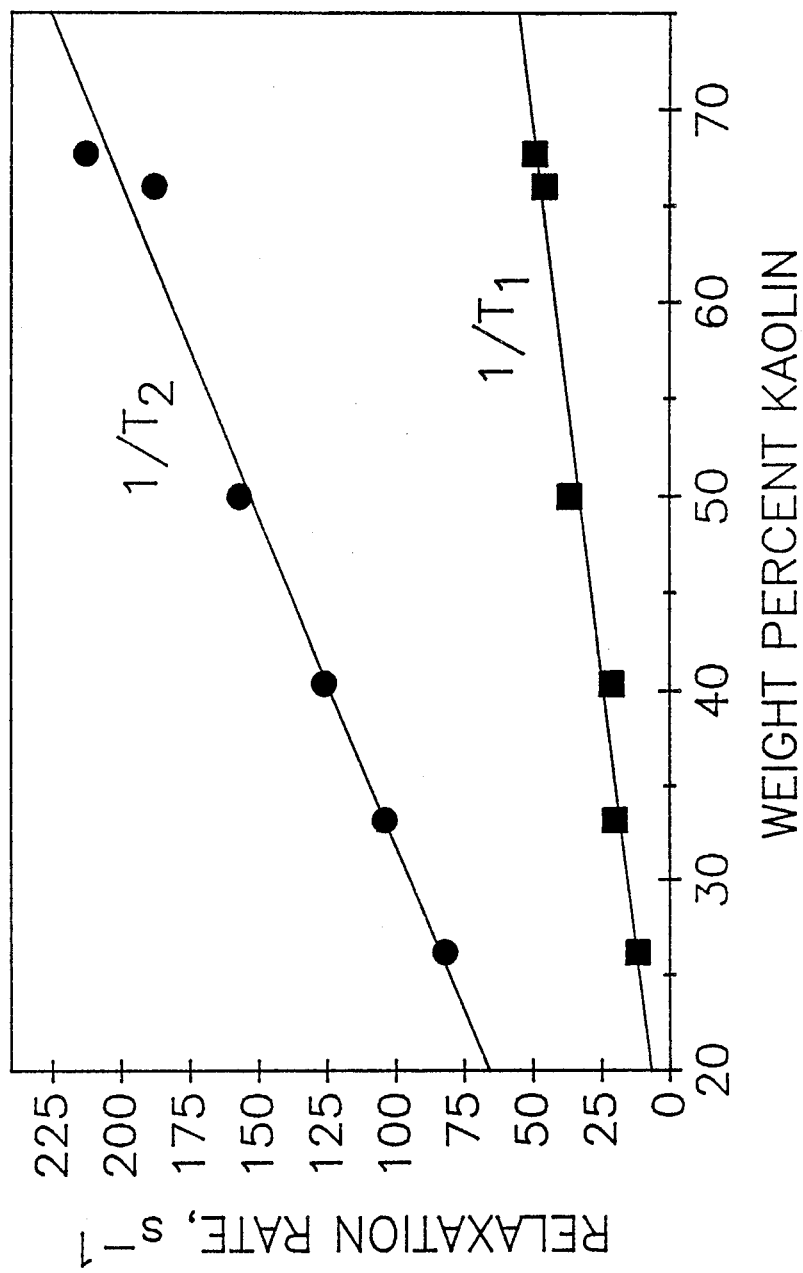
FIG. 1 is a graph showing transverse relaxation rate or $1/T_2$ and the longitudinal relaxation rate or $1/T_1$ as a function of kaolin concentration (expressed as weight percent kaolin to water) measured at 27° C.
Figure 2:
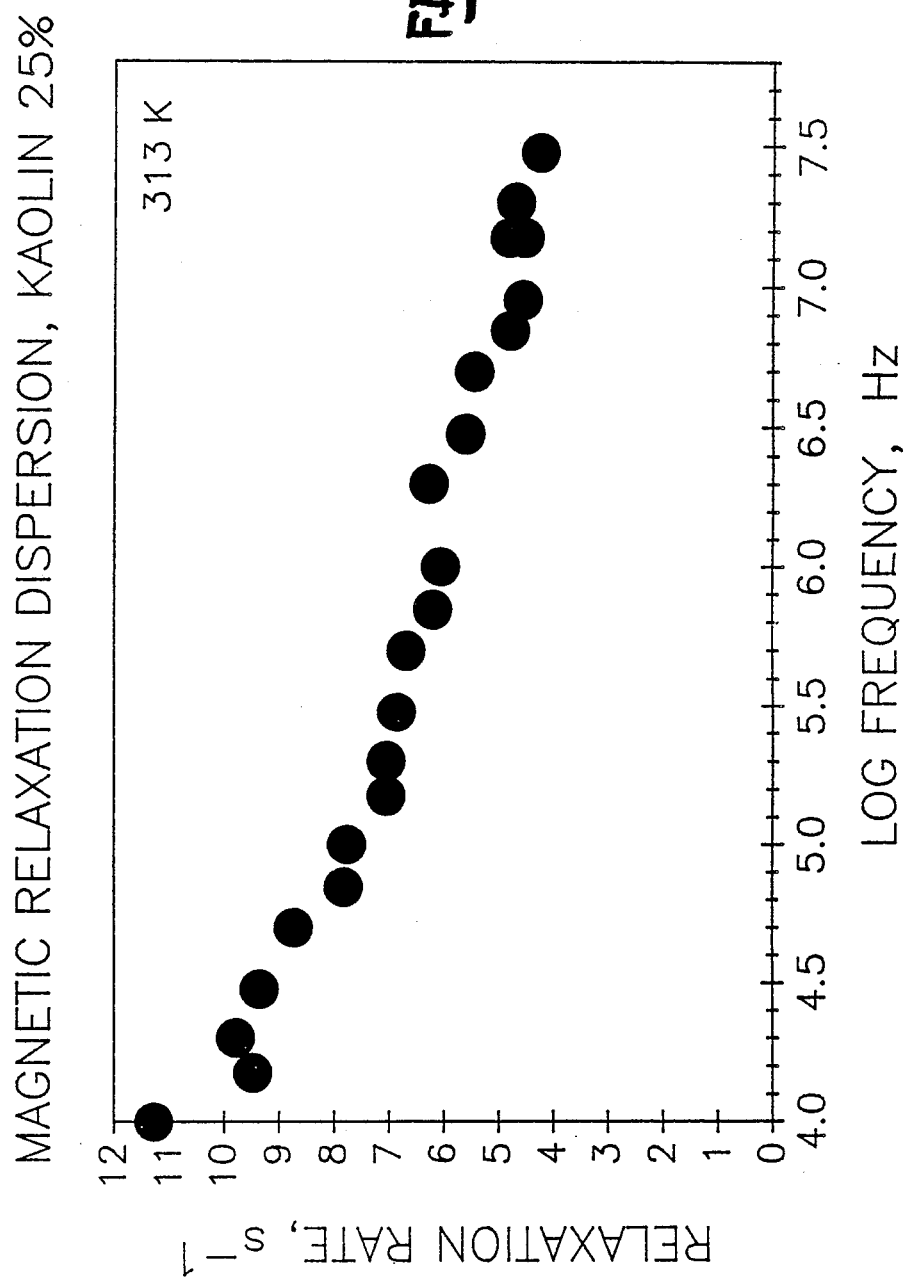
FIG. 2 is a graph of the nuclear magnetic relaxation dispersion for an aqueous suspension (25% kaolin by weight to water at 40° C.) expressed as relaxation rates, seconds⁻ as a function of the proton Larmor frequency (log of the frequency in Hz).

Kaolinite is an effective agent for relaxing water spins as indicated by the data in FIGS. 1 and 2. The preparations in this case are simple aqueous suspensions of kaolin. The relaxation efficiency compared with paramagnetic materials is not high, but since the toxicity is unmeasurably low, the amount of material necessary for effective imaging applications is not a concern. The data in FIG. 1 demonstrate that the transverse relaxation rates are greater than the longitudinal relaxation rates, though both are affected. Thus, the clay minerals will find their primary application in the effects that they exert on the transverse relaxation rates, and imaging sequences that wish to exploit their effects will be so called $T_2$ weighted images. Especially useful clay materials other than kaolinite are montmorillonites, bentonite, hectorite, beidellite, saconite and nontronite.

A second important feature of the relaxation induced by these materials is demonstrated by FIG. 2, which shows the longitudinal or spin lattice relaxation rate as a function of the magnetic field strength for a kaolin suspension. The field dependence is weak, the practical consequence of which is that the material will be effective as a relaxation agent at all currently used clinical magnetic imaging fields.

The kaolin mineral is a primary constituent of the commercial preparation known as Kaopectate, a common over the counter drug thought to be useful for the treatment of diarrhea. Kaopectate consists of a suspension of kaolin and pectin and flavoring ingredients and is manufactured by the Upjohn Company. In images obtained using this preparation as the contrast agent in a human subject, the blackness corresponding to absence of signal is clearly visible in the region where the stomach would normally be imaged. A medically significant aspect of this image is that the pancreas, which is normally obscured by the high intensity associated with the stomach contents and the small bowel, is readily apparent. It is in such applications, e.g., visualization of the pancreas, that these materials will find their primary applications because the composition employed provide strongly contrasting images of the pancreas and stomach.

Figure 3:
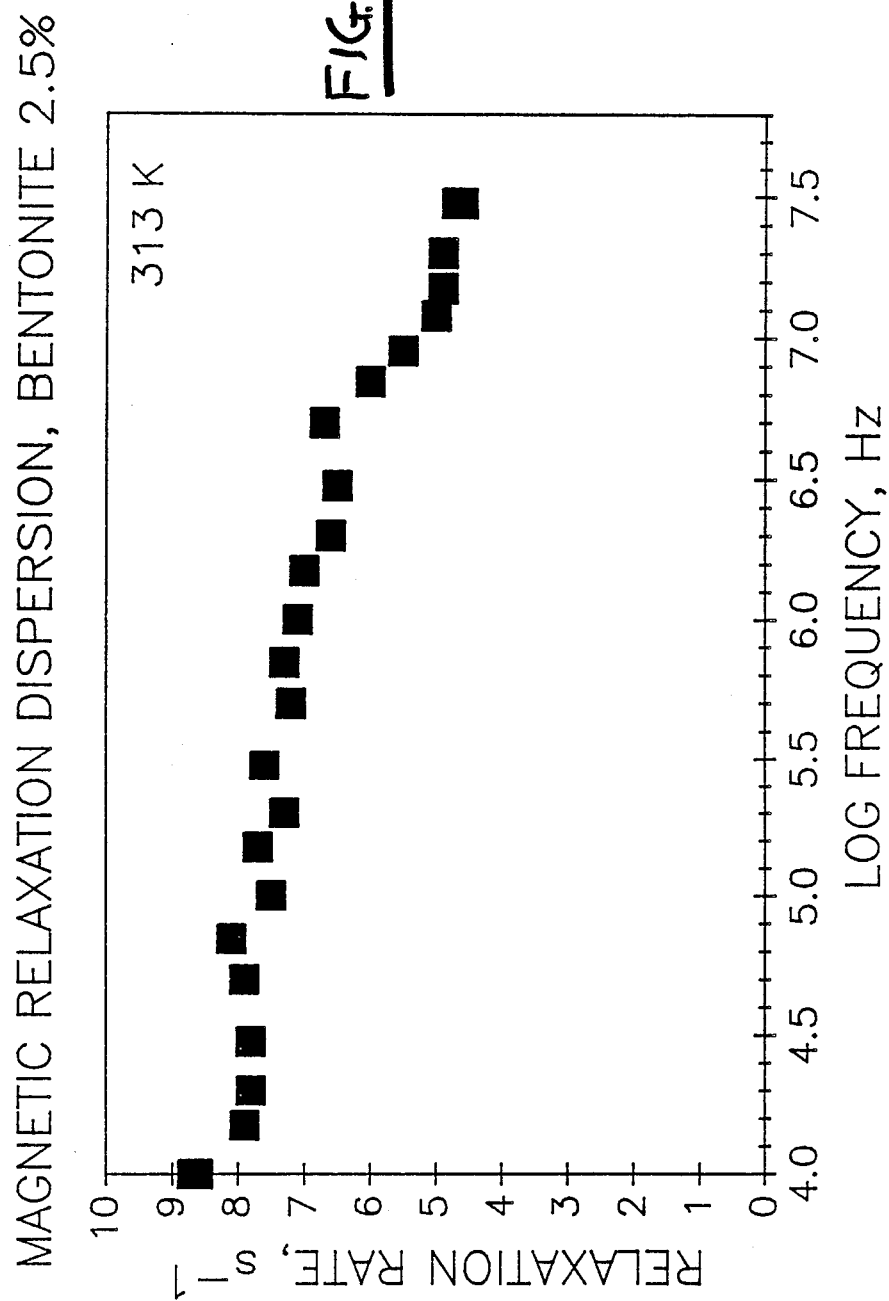
FIG. 3 is a graph similar to FIG. 2 for a 2.5% aqueous suspension of bentonite at 40° C.

The montmorillonites, a representative of which is bentonite, is more efficient in relaxing water proton spins than the kaolin class. An example is indicated in FIG. 3, where the concentration dependence of a preparation of bentonite at 2.5% by weight is shown. The effects on both longitudinal and transverse relaxation rates, $1/T_1$ and $1/T_2$ are clearly significant, and the material is more efficient than the kaolin on a weight basis. There are two obvious benefits of this increased efficiency: (1) the dose or the amount of material needed to provide significant changes in the water proton spin relaxation rates is lower minimizing the possible toxicity if there were any, and minimizing possible unpleasant side effects if there were any; (2) the effects of dilution as an administration to the bowel mixes with contents will be less important because the effects of dilution are far less with the montmorillonites than the kaolinites as shown by FIGS. 1 (for kaolin) and 3 (for bentonite).

The data and clinical example presented above demonstrate that these materials and the procedures normally associated with obtaining a nuclear magnetic resonance image will produce modified images where the fluids in contact with the clay minerals will be eliminated or substantially reduced in intensity in the resulting magnetic image. Though the data of FIGS. 1, 2, and 3 demonstrate that both longitudinal and transverse relaxation times are altered significantly by interactions with these materials, the effects on the transverse relaxation time or $T_2$ are considerably larger than on spin lattice relaxation times or $T_1$. Thus, the preparations of clay minerals will primarily be associated with that class of relaxation agents considered primarily $T_2$ or transverse relaxation agents. By extension, clinical or practical application of this relaxation effect will largely involve selection of image acquisition parameters that will optimize this differential effect on relaxation rates as is routinely done in clinical imaging contexts. That is, the choice of the data acquisition recycle time, commonly called TR and the delay time between the initial excitation and the echo from which the image is reconstructed commonly called TE will be selected to discriminate against short $T_2$ values.

Any suitable buffer to minimize change in gastrointestinal pH may be added to the aqueous clay suspension. Also, a flavoring ingredient can be included.

We claim:

1. In the method of nuclear magnetic resonance imaging of the gastrointestinal tract involving administering a contrast agent, the improvement comprising the oral or rectal administration of a contrast agent consisting essentially of a suspension of clay mineral in water.

2. The method of nuclear magnetic resonance imaging according to claim 1, wherein the improvement further comprises measuring the long transverse relaxation times to obtain a $T_2$ weighted image.

3. The method according to claim 1 wherein the clay mineral is kaolin.

4. The method according to claim 1 wherein the clay mineral is one of the montmorillonite class of clay minerals.

5. The method according to claim 1 wherein the clay mineral consists of at least one clay mineral selected from the group consisting of montmorillonite, bentonite, hectorite, beidellite, sauconite and nontronite.

6. The method according to claim 1 wherein the contrast agent also includes a buffer, a flavoring agent, or both.

7. The method according to claim 1 wherein the contrast agent is characterized as providing an image of the stomach or duodenum or bowel and an image of the pancreas, which images stand out in contrast with each other.

* * * * *